United States Patent [19]

Palestrant

[11] Patent Number: 5,102,391
[45] Date of Patent: Apr. 7, 1992

[54] GUIDANCE DEVICE FOR C. T. GUIDED DRAINAGE AND BIOPSY PROCEDURES

[76] Inventor: Aubrey Palestrant, 6800 N. 47th St., Paradise Valley, Ariz. 85253

[21] Appl. No.: 479,349

[22] Filed: Feb. 13, 1990

[51] Int. Cl.⁵ .............................................. A61M 5/00
[52] U.S. Cl. ........................... 604/116; 128/DIG. 26; 606/108; 33/512
[58] Field of Search ....................... 604/116; 606/108; 128/DIG. 26; 33/391, 511, 512

[56] References Cited

U.S. PATENT DOCUMENTS

| | | | |
|---|---|---|---|
| 1,451,507 | 4/1923 | Harris et al. | 33/391 |
| 2,451,183 | 10/1948 | Tantimonaco | 128/133 |
| 2,490,432 | 10/1946 | Hubbard | 128/216 |
| 3,135,263 | 6/1964 | Connelley, Jr. | 33/512 |
| 4,058,114 | 10/1977 | Soldner | 128/2 V |
| 4,212,297 | 7/1980 | Johnson, Jr. et al. | 128/207.14 |
| 4,341,220 | 7/1982 | Perry | 128/630 |
| 4,583,538 | 4/1986 | Onik et al. | 128/303 B |
| 4,592,352 | 6/1986 | Patil | 128/303 B |
| 4,669,195 | 6/1987 | Griffin | 33/591 |
| 4,723,544 | 2/1988 | Moore et al. | 604/116 |
| 4,733,661 | 3/1988 | Palestrant | 128/303 B |
| 4,883,053 | 11/1989 | Simon | 128/DIG. 26 |

OTHER PUBLICATIONS

Frederick et al., "A Light-Guidance System to be Used for CT-Guided Biopsy", *Radiology*, vol. 154, No. 2, Feb. 1985, pp. 535-536.

Hruby et al., "A New Device for CT-Guided Biopsy and Puncture: Experimental and Clinical Data", Scientific Program of the *Radiological Society of North American*, Dec. 1986, *Works in Progress-General Diagnosis Abstracts*, vol. 161 (p), p. 347.

*Primary Examiner*—Gene Mancene
*Assistant Examiner*—Michael Lynch
*Attorney, Agent, or Firm*—Cahill, Sutton & Thomas

[57] ABSTRACT

A guidance device for use in performing C.T. guided needle loaded catheter drainage and needle biopsy procedures includes a needle or catheter support to which the needle or catheter is releasably fastened. A pendulum pivotally depends from a pivot point on the catheter support under the force of gravity. A protractor is secured to either the catheter support or the depending pendulum to indicate the relative angular relationship between the catheter and the pendulum, and thereby indicate the angle formed between the catheter and either a horizontal or vertical axis. Having previously determined the angle at which the catheter is to be inserted into the patient's body, the user rotates the angular position of the catheter until the protractor reading matches the desired angle.

14 Claims, 2 Drawing Sheets

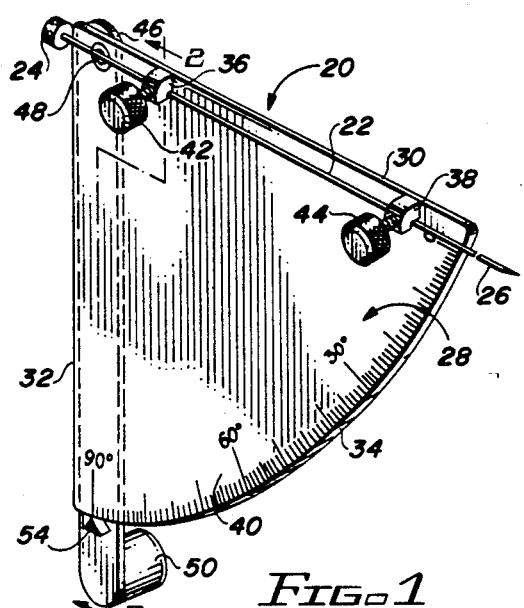
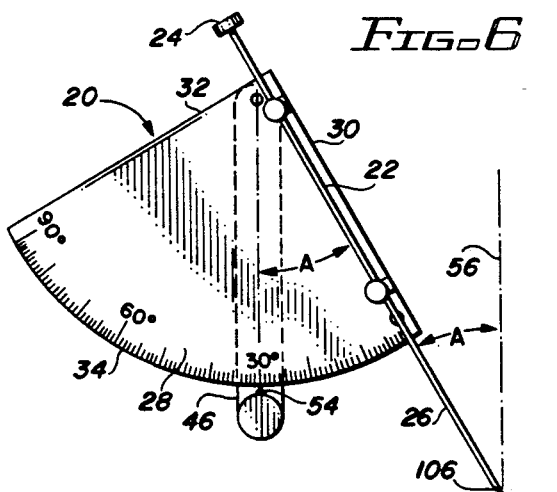
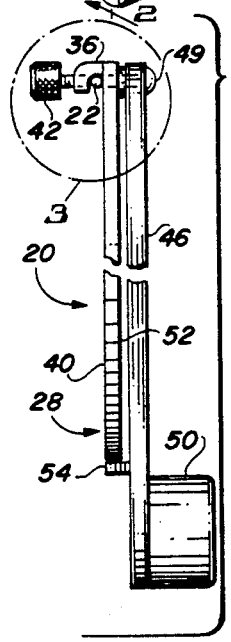
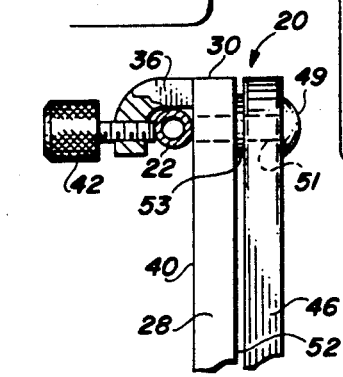
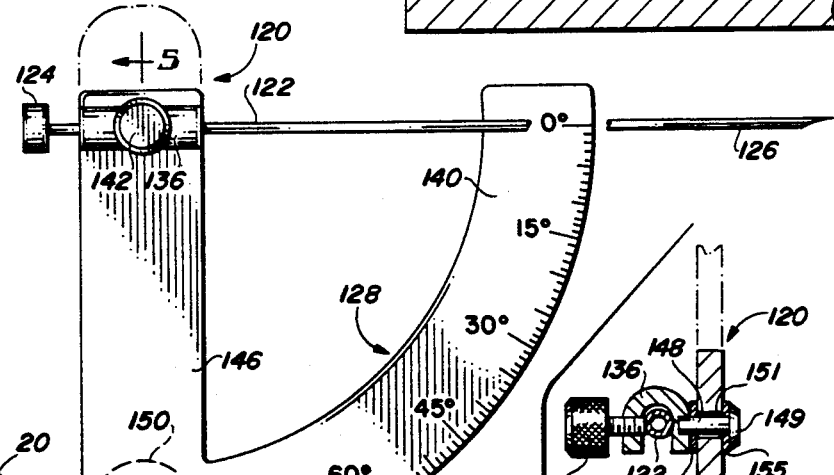
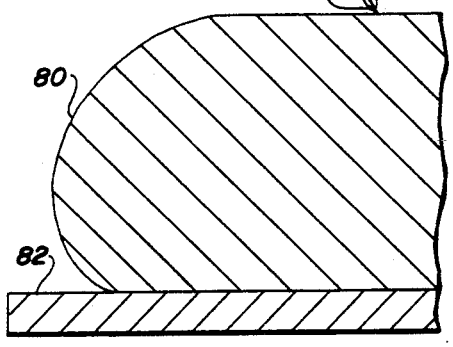
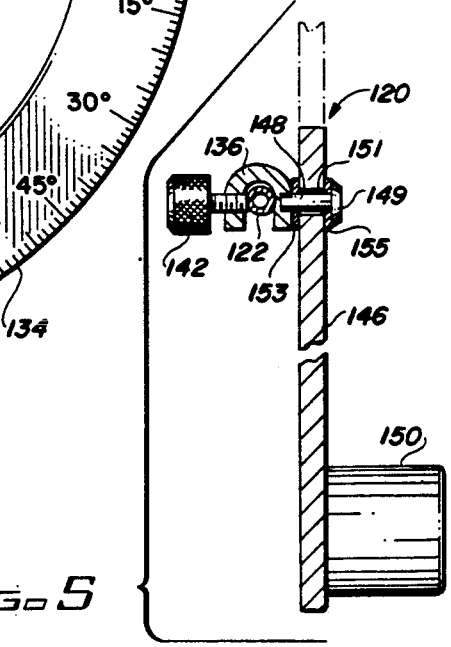

GUIDANCE DEVICE FOR C. T. GUIDED DRAINAGE AND BIOPSY PROCEDURES

FIELD OF THE INVENTION

The present invention relates generally to apparatus for guiding a catheter or needle to a preselected point within a patient's body, and more particularly, to an improved guidance device for guiding biopsy needles, drainage catheters and the like, into a patient's body in conjunction with a C.T. scanner.

DESCRIPTION OF THE PRIOR ART

In recent years, total body C.T. scanners have become commonly used to provide doctors with a cross-sectional picture of a patient's internal organs and tissues. This imaging modality can define abnormal tissues but, in many situations, cannot determine what has caused the abnormality. Through the use of C.T. scanner technology, physicians are able to accurately place biopsy needles and drainage catheters into abnormal tissues with a high degree of success and with a low morbidity and mortality to the patient. This approach has changed the way in which medical diagnoses are made. For example, exploratory laparotomies for suspected tumors have decreased significantly in recent years in view of the increasing use of C.T. guided biopsies of suspicious masses in the abdomen.

C.T. scanners that are presently available are capable of measuring a proposed trajectory for a biopsy needle or drainage catheter to within 0.1 millimeters with respect to depth, and within 0.1 degree with respect to angular orientation. However, there is no known apparatus available, apart from the apparatus disclosed in applicant's U.S. Pat. No. 4,733,661, which can accurately and easily utilize such information to properly position a biopsy needle or drainage catheter relative to the patient's body. To the applicant's knowledge, most physicians perform C.T. guided procedures by initially positioning the needle or catheter at a rough estimation of the desired angle, and by then slowly advancing the needle or catheter into the patient's body, taking numerous C.T. scans along the way to determine the actual position of the needle or catheter, and altering its trajectory as needed. This trial and error technique has major disadvantages. First, it usually requires a relatively long period of time and causes the patient to remain in a fixed position which most patients find uncomfortable. Secondly, additional radiation may be harmful to the patient. Additionally, in institutions where C.T. access is limited, a lengthy procedure may excessively utilize the available time, preventing other patients from being studied.

C.T. scanner guided stereotactic brain surgery is known in the art, and various patents disclose frames for attachment to a patient's head for performing a stereotactic surgical procedure. Such stereotactic surgical apparatus for use in conjunction with C.T. scanners is disclosed in U.S. Pat. Nos. 4,341,220 and 4,592,352. The brain, because of its consistent relationship to the boney skull, can have a rigid frame attached to it which can then provide the needed reference coordinates from which various paths can be calculated. However, with respect to other parts of the body, underlying organs and tissues do not bear a constant relationship to the surface anatomy. In addition, parts of the body other than the head lack a sufficiently rigid structure to which a stereotactic frame can be reliably attached.

U.S. Pat. No. 4,058,114 to Soldner discloses a guide aide designed to introduce a puncturing cannula into the body under the guidance of ultrasound imaging equipment. The disclosed apparatus requires that the guide aide be secured to the ultrasound transducer. The disclosed apparatus further requires a targeting aide fastened to the ultrasound image viewing screen. The ultrasound transducer rests upon the patient's body and provides a support for the guide aide. In contrast, C.T. scanners do not utilize a transducer in contact with the patient's body, and accordingly, the guide aide and targeting aide disclosed by Soldner could not be used in conjunction with C.T. guided interventional procedures.

U.S. Pat. No. 4,583,538 issued to Onik et al. discloses an apparatus designed to facilitate C.T. guided biopsies of the body. The stereotaxis guide instrument disclosed in this patent is floor-mounted and is designed to position a needle guide by moving the same through any of three perpendicular axes. Angular rotations about such axes are permitted to orient the needle guide in any desired direction. However, the articulated arm configuration disclosed by Onik et al. requires the user to manipulate a great number of cranks, bearings, and arms before a needle can be inserted into the patient.

C.T. scanners are adapted to project a laser-generated longitudinal reference beam along the central longitudinal axis of the scanning table. This longitudinal reference beam serves to designate, upon the patient's body, the vertical axis of all scanned images generated by the C.T. scanner. C.T. scanners are also adapted to project a first laser-generated transverse reference beam within the gantry of the scanner and perpendicular to the longitudinal reference beam to indicate the actual portion of the patient's body through which a scan is being taken. A second transverse reference beam is also projected by the C.T. scanner outside the gantry and parallel to the first transverse beam and spaced therefrom by a predetermined distance. Once a target area in the patient's body has been scanned, the scanning table can be moved along the longitudinal axis by the predetermined distance to cause the second transverse beam to illuminate the same portion of the patient's body that was previously illuminated by the first transverse beam before the scanning table was moved.

Within U.S. Pat. No. 4,733,661, the present applicant disclosed a guidance device for C.T. guided drainage and biopsy procedures which uses the depth and angular orientation information provided by the C.T. scanner, and which permits a physician or other user to accurately perform a C.T. guided interventional procedure within a patient's body with relative ease A base is provided with a bubble level to allow the user to verify that the base is horizontal A needle support arm is pivotally coupled to the base, and a protractor indicates the angle formed between the base and the needle support arm. The needle support arm is locked at the desired angle, and the user slides the needle along the support arm into the patient's body while holding the base level and maintaining the needle within the vertical plane defined by the transverse laser light beam projected by the C.T. scanner.

While the device disclosed in applicant's aforementioned U.S. Pat. No. 4,733,661 is a significant improvement over other previously known guidance devices, it does require two-handed operation; one of the user's hands must be used to steady the base in a horizontal plane in accordance with the bubble level indication, and a second hand must be used to advance the catheter along the support arm into the patient's body. This requirement for the use of both hands imposes limitations on the user which are preferably avoided. Moreover, while the device may be convenient to right-handed users, the applicant believes that it is less convenient to left-handed users. In addition, while such device is relatively inexpensive and simple to make and use, it is always desireable to further minimize the cost of manufacture and to maximize the ease of use of such a device.

Accordingly, it is an object of the present invention to provide a guidance device which allows a physician or other user to perform a C.T. guided interventional procedure within a patient's body more accurately, more easily and more expeditiously than apparatus known or used in the past to perform such procedures.

It is another object of the present invention to provide such a guidance device which eliminates the need to make repeated C.T. scans in order to insure that the biopsy needle or drainage catheter is correctly aimed toward the target area.

It is still another object of the present invention to provide such a guidance device which allows a physician or user to easily transfer the accurate angle measurements obtained from the C.T. scanner to a patient in order to direct the biopsy needle or drainage catheter to the desired target area when performing a C.T. guided interventional procedure.

It is a further object of the present invention to provide a guidance device which continuously displays the angular orientation of the needle, relative to a horizontal or vertical axis, as it passes into the patient, thereby allowing the user to immediately correct any variations from the desired angle.

It is a still further object of the present invention to provide such a guidance device which minimizes required manipulation of the needle during insertion and thereby prevents unwanted complications such as bleeding.

Yet another object of the present invention is to provide such a guidance device which may be operated with one hand.

Still another object of the present invention is to provide such a guidance device which can easily be removed from the needle once the target area has been reached, and the biopsy or drainage is about to be performed.

An additional object of the present invention is to provide such a guidance device which is of simple and inexpensive construction, and which may be easily sterilized before use.

These and other objects of the present invention will become more apparent to those skilled in the art as the description thereof proceeds.

SUMMARY OF THE INVENTION

Briefly described, and in accordance with the preferred embodiments thereof, the present invention relates to a hand-held guidance device allowing a user to accurately place a biopsy needle, trocar loaded drainage catheter, or the like within a body of a patient, and which provides a continuous indication of the angular relationship between the longitudinal axis of the catheter and either a horizontal or vertical axis. A guide, in the form of a catheter support, is adapted to releasably receive the catheter. A pendulum pivotally depends from the catheter support at a pivot point and is adapted to hang vertically therefrom. Indicia, in the form of angle markings, are provided upon either the catheter support or the pendulum for indicating the angular relationship between the longitudinal axis of the catheter and the pendulum, thereby indicating the angular relationship between the catheter and a horizontal or vertical axis.

In one preferred form, the catheter support includes supporting brackets, screw clamps, hooks, spring clamps or similar mechanisms for releasably fastening the catheter to the catheter support and maintaining the catheter parallel to a predetermined path the catheter support along. The catheter support includes a protractor with said indicia provided thereon and extending substantially parallel to the pendulum. As the angular position of the catheter support is rotated by the user, the pendulum sweeps across the protractor for continuously indicating the angle formed between the catheter and either the horizontal or vertical axis. Preferably, the catheter is secured to a first face of the protractor, while the pendulum extends along a second opposing face thereof.

According to a second form of the present invention, a protractor is secured to the pendulum. The catheter support releasably receives the proximal end of the catheter and supports the catheter substantially parallel to a face of the protractor for causing the distal end of the catheter to sweep across the face of the protractor when the catheter support is rotated about the pivot point. The catheter support may be in the form of a semicylindrical sleeve, and a threaded screw clamp or similar device may be used to releasably fasten the catheter therein. Indicia provided upon the protractor indicate the angle formed between the catheter and either the horizontal or vertical axis. The pendulum is supported about a pivot axis, and the catheter preferably has its longitudinal axis perpendicular to, and substantially co-planar with, the pivot axis.

BRIEF DESCRIPTION OF THE DRAWINGS

FIG. 1 is a perspective view of a first embodiment of a catheter guidance device constructed in accordance with the teachings of the present invention.

FIG. 2 is a sectional view of the guidance device shown in FIG. 1, taken through the lines designated 2—2 within FIG. 1.

FIG. 3 is an enlarged view of the catheter retaining portion of the guidance device as shown within the dashed circle 3 within FIG. 2.

FIG. 4 is a front view of a second embodiment of the present invention having a pendulum with a protractor incorporated therein.

FIG. 5 is a cross-sectional view of the guidance device shown in FIG. 4, taken through the plane indicated by lines 5—5 within FIG. 4.

FIG. 6 is a front view of the guidance device shown in FIG. 1 as it might be used in guiding a catheter into the body of a patient.

DETAILED DESCRIPTION OF THE PREFERRED EMBODIMENTS

Figure 7:
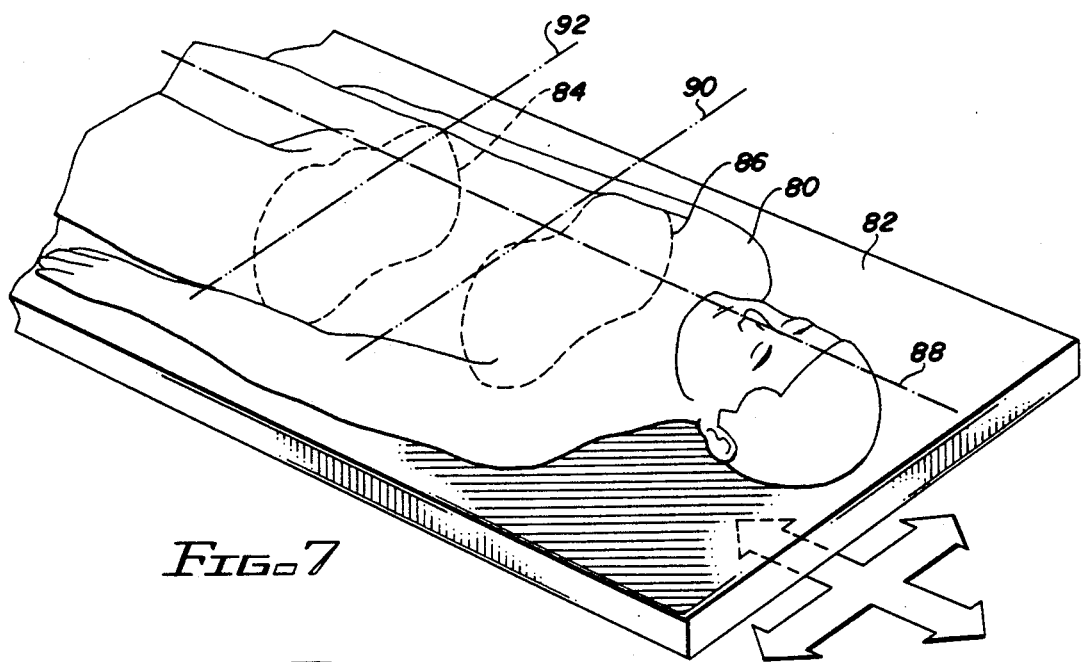
FIG. 7 is a perspective view of a C.T. scanning table for supporting a patient and indicating, in dashed lines, the paths of various laser light reference beams projected upon the patient's body by the C.T. scanner.

With reference to FIG. 1, a guidance device is identified generally by reference numeral 20 and is adapted to allow a user to accurately place a biopsy needle, trocar loaded drainage catheter, or the like within the body of a patient along a desired angular trajectory. As used herein, the term "catheter" should be understood to apply equally to biopsy needles, drainage catheters and similar devices that are routinely inserted into a patient's body when a physician or other user performs a C.T. guided interventional procedure. Within FIG. 1, catheter 22 includes a proximal end or hub 24 and a distal end 26. Guidance device 20 includes a protractor 28 preferably formed of transparent plexiglass. Protractor 28 includes an upper edge 30, a side edge 32 extending perpendicular to upper edge 30, and an arcuate edge 34 extending through a ninety degree arc between upper edge 30 and side edge 32.

The upper portion of protractor 28 in proximity to upper edge 30 serves as a catheter support for releasably receiving catheter 22. As shown in FIGS. 1-3, a pair of hook-shaped brackets 36 and 38 are secured along a first face 40 of protractor 28 along upper edge 30 thereof. Clamp screws 42 and 44 threadedly engage brackets 36 and 38, respectively, for releasably clamping catheter 22 against first face 40 of protractor 28. Thus, brackets 36 and 38, and clamp screws 42 and 44, collectively serve as a means for releasably fastening catheter 22 proximate to, and parallel to, the upper edge 30 of protractor 28. Preferably, catheter 22 is fastened to protractor 28 with hub 24 proximate to side edge 32, thereby permitting distal end 26 to extend beyond protractor 28; protractor 28 thereby avoids interference with the patient's body as the tip of the catheter is inserted into the patient's body.

As shown in FIGS. 1-3, a pendulum 46 pivotally depends from protractor 28 about a pivot point 48 near the upper end of pendulum 46. The lower end of pendulum 46 has a weight 50 secured thereto for causing pendulum 46 to hang vertically from pivot point 48 under the force of gravity. A pivot pin 49 extends through an aperture 51 formed in the upper end of pendulum 46 and is fastened to protractor 28. A spacing washer 53 (see FIG. 3) is interposed between pendulum 46 and protractor 28 to minimize any friction therebetween. Pendulum 46 may also be made of plexiglass, and weight 50 may comprise a cylindrical portion of plastic cemented to the lower end of pendulum 46. As shown in FIGS. 1-3, pendulum 46 is preferably supported to extend along second face 52 of protractor 28 opposite first face 40 thereof. In this manner, pendulum 46 avoids any interference with catheter 22. Pendulum 46 is preferably of a length that is slightly greater than the length of edges 30 and 32 of protractor 28.

As shown in FIGS. 1 and 2, a pointer 54 projects outwardly from pendulum 46 just beyond arcuate edge 34 of protractor 28. Indicia in the form of angle markings are printed along arcuate edge 34 of protractor 28 through an arc of ninety degrees, at one degree intervals. A first set of numerals are printed at zero degrees, thirty degrees, sixty degrees, and ninety degrees for indicating the angle formed between catheter 22 and pendulum 46, and hence between catheter 22 and a vertical axis. Pointer 54 of pendulum 46 initially lies opposite the ninety degree marking of protractor 28 as shown in FIG. 1, indicating that catheter 22 is initially at a ninety degree angle relative to a vertical axis. As guidance device 20 is rotated toward the position shown in FIG. 6, pendulum 46 sweeps across face 52 of protractor 28 and continuously indicates the angle formed between catheter 22 and a vertical axis. Within FIG. 6, it will be noted that the angle A indicated between catheter 22 and pendulum 46 is the same as angle A formed between catheter 22 and vertical axis 56. Thus, rotation of the angular position of guidance device 20 about pivot point 48 until pointer 54 lies opposite the thirty degree marking insures that catheter 22 will enter the patient 80 at an angle of thirty degrees to the vertical.

Referring to FIG. 1, the zero degree marking lying closest to arcuate edge 34, if extended toward edge 32 of protractor 28, would pass through pivot point 48. Similarly, the ninety degree marking lying closest to arcuate edge 34, if extended upwardly toward edge 30 of protractor 28, would also intersect pivot point 48. The releasable fastening means formed by brackets 36 and 38, and screw clamps 42 and 44, maintains catheter 22 parallel to the line intersecting pivot point 48 and the zero degree marking lying closest to arcuate edge 34. The aforementioned line intersecting pivot point 48 and the zero degree marking lying closest to arcuate edge 34 may be regarded as a predetermined path along the catheter support, and catheter 22 is maintained parallel thereto.

Still referring to FIG. 1, a second set of numerals is printed upon first face 40 of protractor 28, ranging from zero degrees to ninety degrees, such second set of numerals lying further from arcuate edge 34 than the first set of numerals already described. This second set of numerals compliments the first set of numerals and, in conjunction with pointer 54, indicates the angle formed between catheter 22 and a horizontal axis.

FIGS. 4 and 5 show an alternate embodiment of the present invention wherein the protractor is supported by the pendulum. In FIG. 4, the guidance device is designated generally by reference numeral 120, and is shown supporting catheter 122. Catheter 122 includes a hub portion 124 at its proximal end and further includes a distal end 126. A catheter support, or guide means, is provided in the form of an inverted U-shaped semicylindrical sleeve 136. A threaded screw clamp 142 threadedly engages sleeve 136 for releasably clamping catheter 122 therein. A pendulum 146 pivotally depends from sleeve 136 about a pivot point 148 coaxial with pivot pin 149. Pivot pin 149 extends along a pivot axis through an aperture 151 formed within the upper end of pendulum 146. Spacer washers 153 and 155 may be interposed between pendulum 146 and sleeve 136, and between pendulum 146 and the head of pivot pin 149, respectively, to minimize friction therebetween. A weight 150 is secured to the lower end of pendulum 146. Accordingly, pendulum 146 freely pivots relative to sleeve 136 and is adapted to hang vertically therefrom.

Extending upwardly from the lower end of pendulum 146 is an arcuate member forming a protractor 128 and including a face 140. Protractor 128 and pendulum 146 are preferably integral with one another and formed of transparent plexiglass. Indicia in the form of angular markings are printed upon face 140 along the outer arcuate edge 134 of protractor 128. The marking designated as ninety degrees, if extended upwardly, would pass through pivot point 148. Weight 150 is positioned on pendulum 146 in a manner which causes the 90 degree marking to be directly below the pivot point. Similarly, the horizontal marking designated zero degrees, if extended to the left (relative to FIG. 4), would also pass through pivot point 148.

As shown in FIG. 4, sleeve 136 and screw clamp 142 releasably receive the proximal end of catheter 122 near hub 124. Sleeve 136 supports catheter 122 to extend substantially parallel to face 140 of protractor 128. In addition, sleeve 136 releasably supports catheter 122 in a manner which maintains the longitudinal axis of catheter 122 perpendicular to, and substantially co-planar with, the pivot axis of the pendulum. Accordingly, as the angular position of catheter 122 is rotated about pivot point 148 by the user, the distal end 126 of catheter 122 sweeps across face 140 of protractor 128. The intersection between catheter 122 and the indicia printed upon face 140 of protractor 128 indicates the angle formed between catheter 122 and a horizontal axis. Those skilled in the art will appreciate that a second set of complimentary numerical degree angles may also be printed upon face 140 of protractor 128 to indicate the relative angular relationship between catheter 122 and a vertical axis.

As noted above, the guidance device should be easily disengaged from the catheter once the catheter is properly placed within the patient's body. For example, a physician or other user of the guidance device would probably find it difficult to efficiently operate a biopsy needle in order to obtain a tissue sample if the needle remained engaged with the guidance device. Accordingly, catheter 22 may easily be released from guidance device 20 of FIG. 1 by simply unscrewing screw clamps 42 and 44 and slightly raising guidance device 20 away from catheter 22. Similarly, guidance device 120 of FIGS. 4 and 5 may easily be disengaged from catheter 122 by unthreading screw clamp 142 and slighting raising guidance device 120 away from catheter 122.

Referring now to FIG. 7, a patient 80 is shown lying upon a movable, computer-controlled scan table 82 of a C.T. scanning system, such as a GE 9800 C.T. scanner commercially available from General Electric, or other high resolution C.T. scanner. Other components of the C.T. scanning system are omitted for clarity. The C.T. scanner is designed to provide a cross-sectional image of the patient's body taken through a vertical scan plane. Two such vertical scan planes are shown in FIG. 5 by dashed lines 84 and 86.

As a reference aide, C.T. scanners include a C.T. lighting system designed to project reference beams of laser light toward the scanning table and upon the patient's body to indicate the portion of the patient's body being scanned. A first transverse beam of laser light, designated by dashed line 90, is projected by the C.T. scanner within the gantry of the scanner (not shown) to indicate the location of the vertical plane through which the patient's body is being scanned. A second transverse beam of laser light, indicated by dashed line 92, is projected by the C.T. scanner outside the scanner gantry a known distance apart from, and parallel to, the first transverse beam 90. This second transverse beam of laser light is provided principally to aid a technician or physician in properly positioning the patient's body for scanning before the scanning table is actually advanced into the scanner. A longitudinal reference beam, indicated by dashed line 88, is projected longitudinally along the center of scanning table 82 to indicate the center point, or vertical axis, of the scanned image. It is often difficult for a physician to insert a biopsy needle within the patient's body without moving the scanning table out of the scanning apparatus. Accordingly, the scanning table 82 may be withdrawn from the scanning apparatus by the known distance separating transverse beams 90 and 92 in order to cause transverse beam 92 to overlie the area of the patient's body that was scanned just immediately prior to the movement of scanning table 82.

To help insure that the biopsy needle, drainage catheter or like device will hit its intended target, it is desirable for the user to maintain the needle or catheter within the vertical plane that was viewed by the C.T. scanner to locate the target. During use of guidance device 20 (or 120), the user maintains catheter 22 (or 122) in alignment with transverse laser light beam 92 (see FIG. 7), thereby insuring that the catheter lies within the vertical plane of the patient's body that was sectioned by the C.T. scanner. When properly aligned, the transverse laser light beam will illuminate the full length of catheter 22 (or 122) before the same is inserted into the patient's body.

Figure 8:
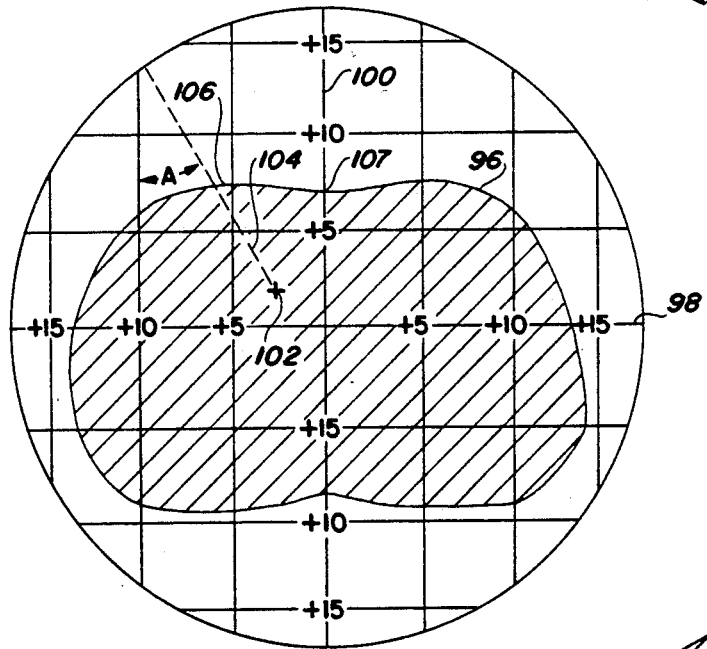
FIG. 8 is a representation of an image projected by a C.T. scanner computer screen and illustrating the manner by which an optimum catheter insertion path may be determined.

In order to use the guidance device of the present invention, a patient is scanned in conventional fashion to determine the location of the abnormal area, also referred to herein as the target area. An image, like that shown in FIG. 8, is displayed upon the C.T. scanner computer screen showing a cross-section of the patient's body. The outline of the displayed image is designated within FIG. 8 by reference numeral 96. By depressing a "grid" button on the monitor console, the computer screen can selectively superimpose an x-axis 98 and a y-axis 100 over the displayed image of the patient's body. Referring briefly to FIG. 7, y-axis 100 corresponds to the position of longitudinal reference beam 88 upon the patient's body For purposes of explanation, it will be presumed that the computer-generated marker designated by reference numeral 102 within the cross-sectional image shown in FIG. 8 designates the tissue mass that is to be biopsied.

While viewing the computer generated image shown in FIG. 8, the physician determines the best straight line path lying within the sectioned plane of the patient's body to reach target 102 without injuring surrounding organs or blood vessels. For the sake of explanation, it will be presumed that the angled path indicated by dashed line 104 represents the selected insertion path for inserting a biopsy needle to reach target area 102. By using a cursor on the computer screen, the physician can mark both the target area 102 and the insertion site 106 at which the needle will be inserted. As shown in FIG. 8, insertion site 106 is the point on the outer surface of the patient's body which is intersected by selected insertion path 104. The C.T. scanner computer can then easily compute the distance from insertion site 106 to the point 107 at which the vertical reference axis, or y-axis 100 intersects the outer surface of the patient's body. The C.T. scanner computer can also be used to display the insertion angle that proposed path 104 forms with either x-axis 98 or y-axis 100. In addition, the C.T. scanner computer is also capable of measuring and displaying the length of the path (i.e., insertion distance) from insertion site 106 to target area 102.

Once the physician has obtained the information set forth above, the physician locates the proposed insertion site upon the patient's body by first moving the scanning table to the position where the scan shown in FIG. 8 was obtained. The physician then measures on the patient's body the distance indicated by the C.T. scanner computer between point 107 and entry site 106. This measurement is made along transverse beam 90 and starts at the intersection of longitudinal light beam 88 and transverse beam 90. It may be sufficient at this stage to simply mark the insertion site 106 upon the patient's body with an indelible pen. However, to insure that the insertion site has been properly located, a 1 mm. radiopaque marker is first placed on this point of the patient's body, and a scan is performed to confirm that the radiopaque marker corresponds to the selected insertion site. The scanning table is then moved along its longitudinal axis by the distance separating transverse beams 90 and 92, thereby shifting the radiopaque marker from the transverse beam 90 to transverse beam 92. The indelible pen is then used to mark the position of the radiopaque marker, and the radiopaque marker is thereafter removed.

Figure 9:
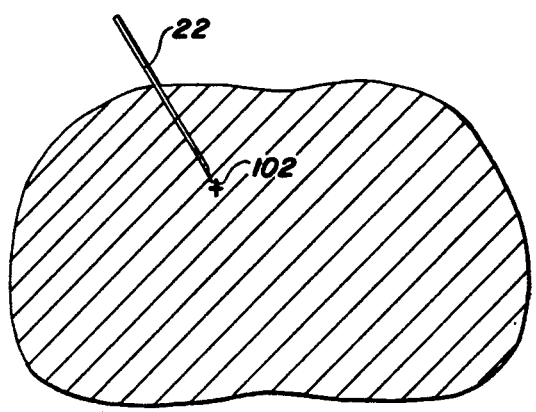
FIG. 9 is a cross-sectional view of the patient's body into which a catheter has been inserted partially along the path indicated by FIG. 8.

Catheter 22 (which may be a biopsy needle) is then inserted into guidance device 20, as shown in FIG. 1. The user then rotates guidance device 20 and catheter 22 until marker 54 of pendulum 46 indicates the desired angle, as previously determined on the computer scanner screen as described above. Catheter 22 is then directed toward the patient's body at the insertion site, as shown in FIG. 6, while the physician simultaneously confirms that transverse reference beam 92 (see FIG. 7) illuminates the full length of catheter 22 (indicating that catheter 22 lies within the sectioned plane) while simultaneously monitoring the angle indicated by marker 54 of pendulum 46. The catheter is advanced into the patient's body 80 at insertion site 106, and catheter 22 is slowly advanced the desired distance toward target area 102 (see FIG. 8). Depending upon the size of lesion or target mass, and its distance from the skin, perhaps one intermediate scan may be desired to ensure that catheter 22 has not been deflected from, and is within, the selected plane and along the proper trajectory. FIG. 9 illustrates such an intermediate scan with catheter 22 advanced to a point just short of target area 102. The manner of using guidance device 120 shown in FIGS. 4 and 5 is substantially identical to the manner of using guidance device 20 as described above.

The guidance device as disclosed herein may be easily manufactured from plexiglass and other inexpensive components which may be easily assembled. The guidance device is relatively compact and may be packaged and stored in sterile form for ready access by physicians or other users. Since the guidance devices disclosed herein are manually supported, the user can quickly position the guidance device for use adjacent the patient's body without the need to adjust a series of cranks, bearings, or arms in order to make the needle insertion. Moreover, both guidance devices 20 and 120 may be operated using a single hand and are therefore equally adapted to left-handed and right-handed users.

Those skilled in the art will now appreciate that a guidance device has been described to facilitate C.T. guided biopsy and fluid drainage in an accurate, easy and relatively prompt manner. While the invention has been described with reference to preferred embodiments thereof, the description is for illustrative purposes only and is not to be construed as limiting the scope of the invention. Various modifications and changes may be made by those skilled in the art without departing from the true spirit and scope of the invention as defined by the appended claims, wherein the term "catheter" is intended to broadly designate biopsy needles, drainage catheters, or any other form of medical needle or tube.

I claim:

1. A hand-held guidance device for allowing a user to accurately place a catheter within the body of a patient, the catheter having a longitudinal axis, said guidance device comprising in combination:
   a) guide means for releasably receiving the catheter;
   b) a pendulum pivotally depending from said guide means; and
   c) indicia provided upon one of either said guide means or said pendulum for indicating the angular relationship between the longitudinal axis of the catheter and said pendulum, and thereby indicating the angular relationship between the longitudinal axis of the catheter and a horizontal or vertical axis.

2. A hand-held guidance device as recited by claim 1 wherein said indicia indicate the angle between the longitudinal axis of the catheter and a vertical axis.

3. A hand held guidance device as recited by claim 1 wherein said indicia indicate the angle between the longitudinal axis of the catheter and a horizontal axis.

4. A hand-held guidance device as recited by claim 1 wherein said catheter support releasably supports the catheter to extend perpendicular to said pivot axis.

5. A hand-held guidance device for allowing a user to accurately place a catheter within the body of a patient, the catheter having a longitudinal axis, said guidance device comprising in combination:
   a) a catheter support including means for releasably fastening the catheter thereto and maintaining the catheter parallel to a predetermined path along said catheter support;
   b) a pendulum coupled to and pivotally depending from said catheter support at a pivot point, said pendulum being adapted to hang vertically from said pivot point; and
   c) indicia provided upon said catheter support for indicating the angular relationship between said predetermined path along said catheter support and said pendulum, thereby indicating the angular relationship between the longitudinal axis of the catheter and a horizontal or vertical axis.

6. A hand-held guidance device as recited by claim 5 wherein said catheter support includes a protractor, said indicia being provided upon said protractor, and said pendulum extending substantially parallel to said protractor for sweeping thereacross as said catheter support is rotated by a user.

7. A hand-held guidance device as recited by claim 6 wherein said protractor includes first and second opposing faces, said means for releasably fastening the catheter being secured to the first face of said protractor, and said pendulum extending along the second face of said protractor.

8. A hand-held guidance device as recited by claim 6 wherein said indicia indicate the angle formed between the predetermined path and said pendulum, and thereby indicate the angle between the longitudinal axis of the catheter and a vertical axis.

9. A hand-held guidance device as recited by claim 6 wherein said indicia indicate the angle formed between said pendulum and a line perpendicular to the predetermined path, and thereby indicate the angle between the longitudinal axis of the catheter and a horizontal axis.

10. A hand-held guidance device as recited by claim 5 wherein said means for releasably fastening the catheter includes a bracket secured to said catheter support for receiving the catheter, and a screw clamp threadedly received by said bracket for releasably clamping the catheter to said catheter support to facilitate removal of said hand-held guidance device from the catheter after the catheter has been inserted into the patient's body.

11. A hand-held guidance device for allowing a user to accurately place a catheter within the body of a patient, the catheter having a longitudinal axis, said guidance device comprising in combination:
   a) a catheter support for releasably receiving a proximal end of a catheter and including means for releasably fastening the catheter to said catheter support;
   b) a pendulum coupled to and pivotally depending from said catheter support at a pivot point along a pivot axis, said pendulum being adapted to hang vertically from said pivot point;
   c) a protractor secured to said pendulum, said protractor include a face having indicia provided thereon;
   d) said catheter support supporting the longitudinal axis of the catheter substantially parallel to the face of said protractor for causing the distal end of the catheter to sweep across the face of said protractor when said catheter support is rotated about said pivot point; and
   e) said indicia indicating the angular relationship between the longitudinal axis of the catheter and a horizontal or vertical axis.

12. A hand-held guidance device as recited by claim 11 wherein said indicia indicate the angle formed between the longitudinal axis of the catheter and a vertical axis.

13. A hand-held guidance device as recited by claim 11 wherein said indicia indicate the angle formed between the longitudinal axis of the catheter and a horizontal axis.

14. A hand-held guidance device as recited by claim 11 wherein said means for releasably fastening the catheter includes a sleeve secured to said catheter support for receiving the catheter, and a screw clamp threadedly received by said sleeve for releasably clamping the catheter to said catheter support to facilitate removal of said hand-held guidance device from the catheter after the catheter has been inserted into the patient's body.

* * * * *